(12) United States Patent
Eury

(10) Patent No.: US 10,709,863 B2
(45) Date of Patent: Jul. 14, 2020

(54) PATIENT CIRCUIT WITH ADJUSTABLE LENGTH

(71) Applicant: KONINKLIJKE PHILIPS N.V., Eindhoven (NL)

(72) Inventor: Matthew Paul Eury, Latrobe, PA (US)

(73) Assignee: Koninklijke Philips N.V., Eindhoven (NL)

(*) Notice: Subject to any disclaimer, the term of this patent is extended or adjusted under 35 U.S.C. 154(b) by 629 days.

(21) Appl. No.: 15/531,001

(22) PCT Filed: Nov. 20, 2015

(86) PCT No.: PCT/IB2015/058999
§ 371 (c)(1),
(2) Date: May 26, 2017

(87) PCT Pub. No.: WO2016/087977
PCT Pub. Date: Jun. 9, 2016

(65) Prior Publication Data
US 2018/0311458 A1    Nov. 1, 2018

Related U.S. Application Data

(60) Provisional application No. 62/087,529, filed on Dec. 4, 2014.

(51) Int. Cl.
*A61M 16/08* (2006.01)
*A61M 16/06* (2006.01)
(Continued)

(52) U.S. Cl.
CPC .... *A61M 16/0875* (2013.01); *A61M 16/0057* (2013.01); *A61M 16/06* (2013.01);
(Continued)

(58) Field of Classification Search
CPC .............. A61M 16/0057; A61M 16/06; A61M 16/0683; A61M 16/08; A61M 16/0875;
(Continued)

(56) References Cited

U.S. PATENT DOCUMENTS 5,454,061 A     9/1995  Carlson
5,517,982 A *   5/1996  Grivas ..................... A62B 7/12
                                                  128/200.24
(Continued)

FOREIGN PATENT DOCUMENTS

JP          200972596 A    4/2009

*Primary Examiner* — Bradley H Philips
(74) *Attorney, Agent, or Firm* — Michael W. Haas

(57) ABSTRACT

An interconnect assembly is for a pressure support system that includes a gas flow generator and a patient interface device fluidly coupled to the gas flow generator. The gas flow generator produces a flow of breathing gas for a patient. The interconnect assembly includes: a conduit fluidly coupled to each of the gas flow generator and the patient interface device, the conduit having a length, and an adjustment assembly including: a number of tension members each at least partially overlaying the conduit, each of the tension members being structured to move independently with respect to the conduit, and a winding apparatus connected to each of the tension members, the winding apparatus being structured to wind each of the tension members. When the winding apparatus winds the tension members, the length of the conduit decreases.

15 Claims, 6 Drawing Sheets

(51) Int. Cl.
*A61M 16/00* (2006.01)
*F16L 11/118* (2006.01)

(52) U.S. Cl.
CPC ............ *A61M 16/08* (2013.01); *F16L 11/118* (2013.01); *A61M 16/0683* (2013.01); *A61M 2209/08* (2013.01)

(58) Field of Classification Search
CPC .... A61M 2209/08; F16L 11/118; F16L 27/12; F16L 27/127
See application file for complete search history.

(56) References Cited

U.S. PATENT DOCUMENTS

| | | | |
|---|---|---|---|
| 5,975,120 A | 11/1999 | Novosel | |
| 6,367,510 B1 | 4/2002 | Carlson | |
| 6,685,713 B1 | 2/2004 | Ahmed | |
| 6,889,688 B1 * | 5/2005 | Wright | B65H 75/406 128/200.24 |
| 7,104,491 B2 * | 9/2006 | Vinding | A61M 39/08 242/378 |
| 2006/0231100 A1 | 10/2006 | Walker | |
| 2007/0045481 A1 | 3/2007 | Adams | |
| 2009/0065005 A1 * | 3/2009 | Ades | A61M 16/06 128/205.25 |
| 2009/0078259 A1 * | 3/2009 | Kooij | A61M 16/0875 128/205.25 |
| 2009/0277454 A1 * | 11/2009 | Davis | A61M 16/0875 128/207.18 |
| 2011/0017856 A1 * | 1/2011 | Penn | A61M 39/08 242/370 |
| 2012/0152931 A1 | 6/2012 | Bohlender et al. | |
| 2014/0299133 A1 * | 10/2014 | Neely | B65H 75/40 128/205.25 |
| 2016/0199613 A1 * | 7/2016 | Hadas | A61M 16/0875 128/202.27 |

\* cited by examiner

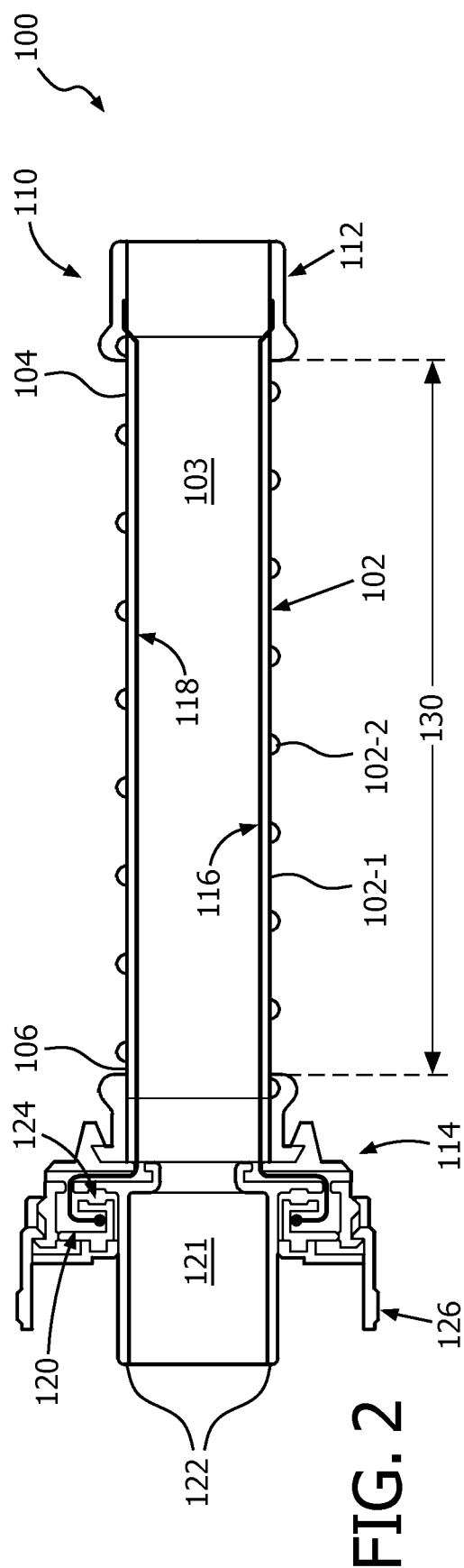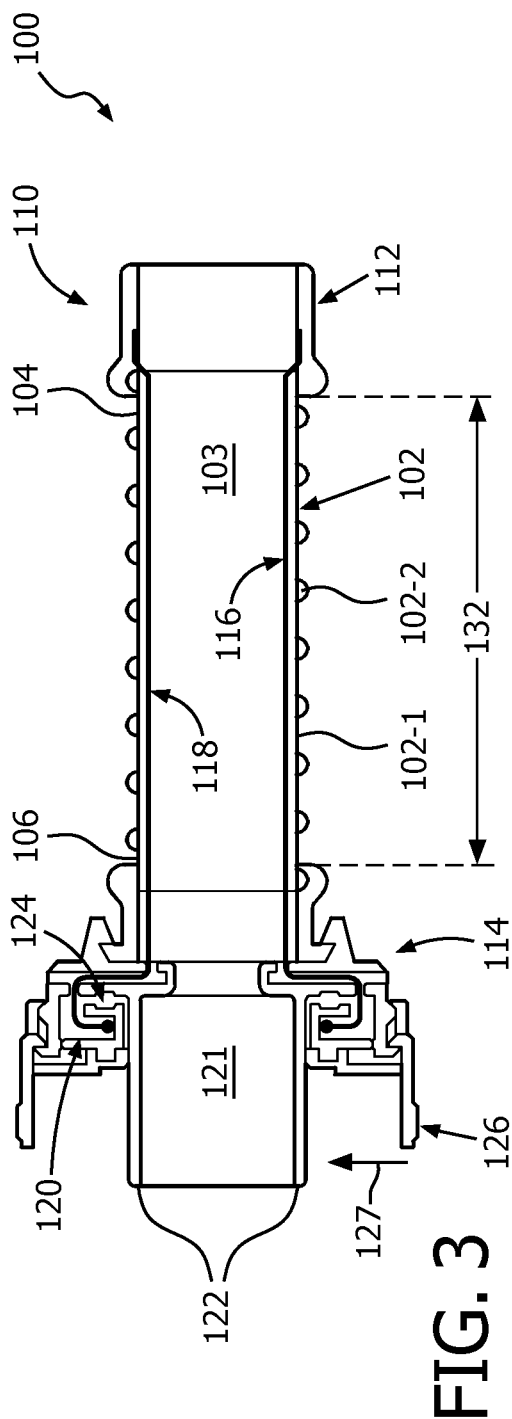

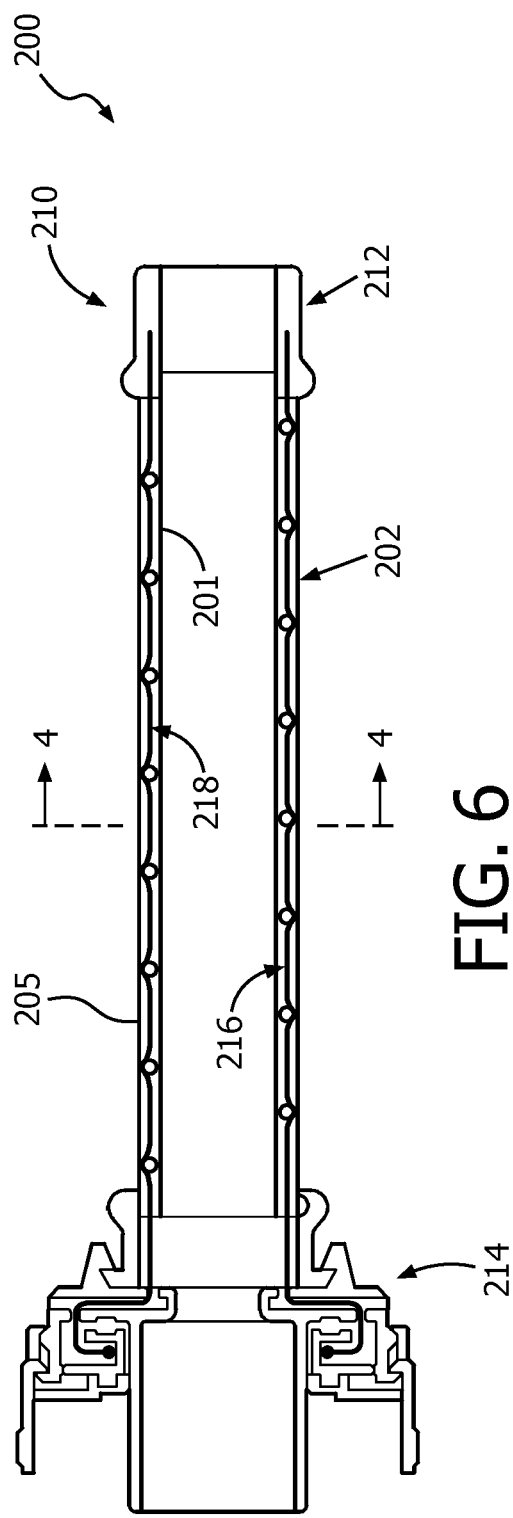
FIG. 6
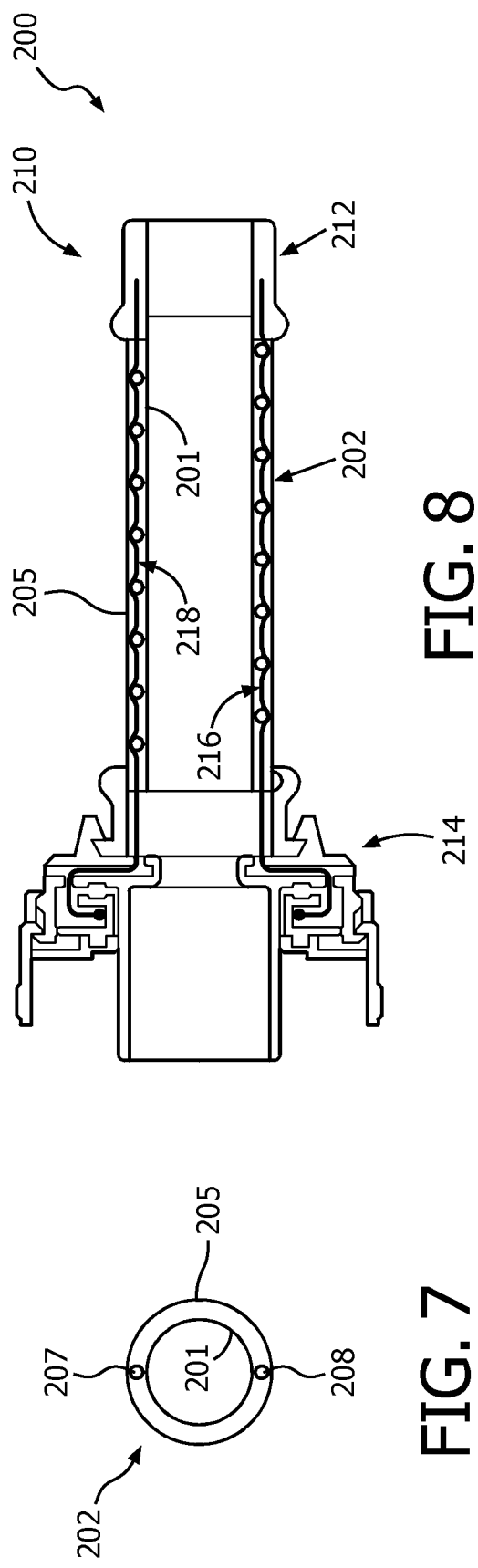
FIG. 8
FIG. 7

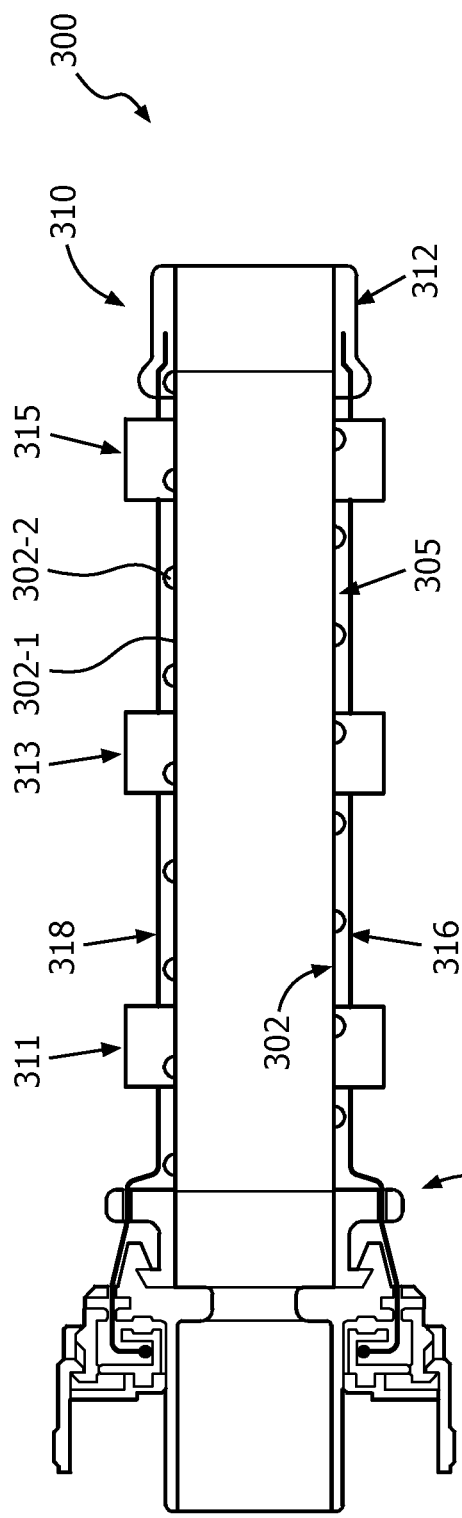
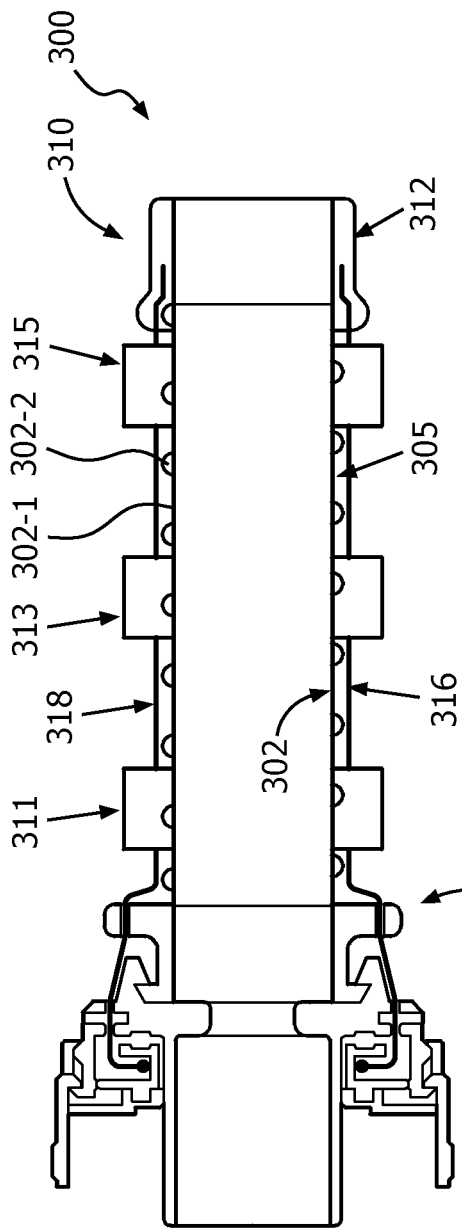
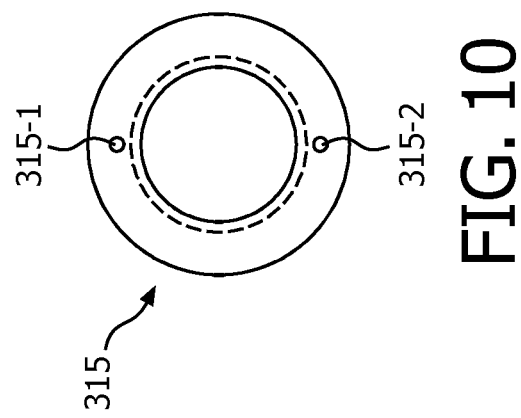
FIG. 9
FIG. 11
FIG. 10

PATIENT CIRCUIT WITH ADJUSTABLE LENGTH

CROSS-REFERENCE TO RELATED APPLICATIONS

This patent application claims the priority benefit under 35 U.S.C. § 371 of international patent application PCT/IB2015/058999, filed Nov. 20, 2015, which claims the priority benefit under 35 U.S.C. § 119(e) of U.S. Provisional Application No. 62/087,529 filed on Dec. 4, 2014, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and, in particular, to pressure support systems including a patient circuit in which the length is adjustable.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces a gas flow generator with the airway of the patient, so that a flow of breathing gas can be delivered from the gas flow generator to the airway of the patient.

Known methods of interfacing the patient interface device with the gas flow generator involve fluidly coupling a conduit (e.g., a patient circuit or hose) to the patient interface device and the gas flow generator. However, such conduits are not customizable. Furthermore, in order to accommodate as many operational situations as possible, such conduits are relatively long. Because many operational situations do not require excessively long conduits, packing and transporting such pressure support systems is undesirably cumbersome.

SUMMARY OF THE INVENTION

In one embodiment, an interconnect assembly for a pressure support system is provided. The pressure support system includes a gas flow generator and a patient interface device fluidly coupled to the gas flow generator. The gas flow generator produces a flow of breathing gas for a patient. The interconnect assembly comprises a conduit (patient circuit) fluidly coupled to each of the gas flow generator and the patient interface device, the conduit having a length and an adjustment assembly. The adjustment assembly comprises at least one, and in one embodiment a number of tension members, each at least partially overlaying the conduit. The tension members are structured to move independently with respect to the conduit, and a winding apparatus connected to each of the tension members, the winding apparatus being structured to wind each of the tension members. When the winding apparatus winds the tension members, the length of the conduit decreases.

In another embodiment, a pressure support system comprises a gas flow generator structured to produce a flow of breathing gas for a patient, a patient interface device fluidly coupled to the gas flow generator, and an interconnect assembly comprising a conduit fluidly coupled to each of the gas flow generator and the patient interface device, the conduit having a length, and an adjustment assembly. The adjustment assembly comprises a number of tension members each at least partially overlaying the conduit, each of the tension members being structured to move independently with respect to the conduit, and a winding apparatus connected to each of the tension members, the winding apparatus being structured to wind each of the tension members. When the winding apparatus winds the tension members, the length of the conduit decreases.

In another embodiment, a method of customizing a pressure support system comprises the steps of: providing the pressure support system, the pressure support system comprising a gas flow generator structured to produce a flow of breathing gas for a patient, a patient interface device fluidly coupled to the gas flow generator, and an interconnect assembly. The interconnect assembly comprises a conduit fluidly coupled to each of the gas flow generator and the patient interface device, the conduit being structured to move between a first position and a second position, the conduit having a first length in the first position and a second length in the second position, the second length being less than the first length, and an adjustment assembly comprising a number of tension members each at least partially overlaying the conduit, each of the tension members being structured to move independently with respect to the conduit, and a winding apparatus connected to each of the tension members, the winding apparatus being structured to wind each of the tension members, winding each of the tension members with the winding apparatus in order to move the conduit from the first position to the second position; and maintaining the conduit in the second position.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 2 is a simplified section view of an interconnect assembly for the pressure support system of FIG. 1, shown with the conduit in the first position;

FIG. 3 is another simplified section view of the interconnect assembly of FIG. 2, shown with the conduit in the second position;

FIG. 6 is a simplified section view of another interconnect assembly that may be implemented in the pressure support system of FIG. 1, shown with the conduit in the first position;

FIG. 7 is a section view of the conduit of the interconnect assembly of FIG. 6, taken along line 4-4 of FIG. 6;

FIG. 8 is another simplified section view of the interconnect assembly of FIG. 6, shown with the conduit in the second position;

FIG. 9 is a simplified section view of another interconnect assembly that may be implemented in the pressure support system of FIG. 1, shown with the conduit in the first position;

FIG. 10 is a side view of a guide member of the interconnect assembly of FIG. 9; and FIG. 11 is another simplified section view of the interconnect assembly of FIG. 9, shown with the conduit in the second position.

DETAILED DESCRIPTION OF THE EXEMPLARY EMBODIMENTS

As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, a "tension member" is a construct that has a maximum length, end-to-end when under tension, but which has, or may have, a reduced length end-to-end when not under tension. "Tension members" include, but are not limited to, braided threads, cables, wires, strings, filaments, and fibers. As employed herein, the term "overlay" shall mean that one component, such as a tension member, includes a portion that extends through, within, or otherwise on another component, such as a conduit.

Figure 1:
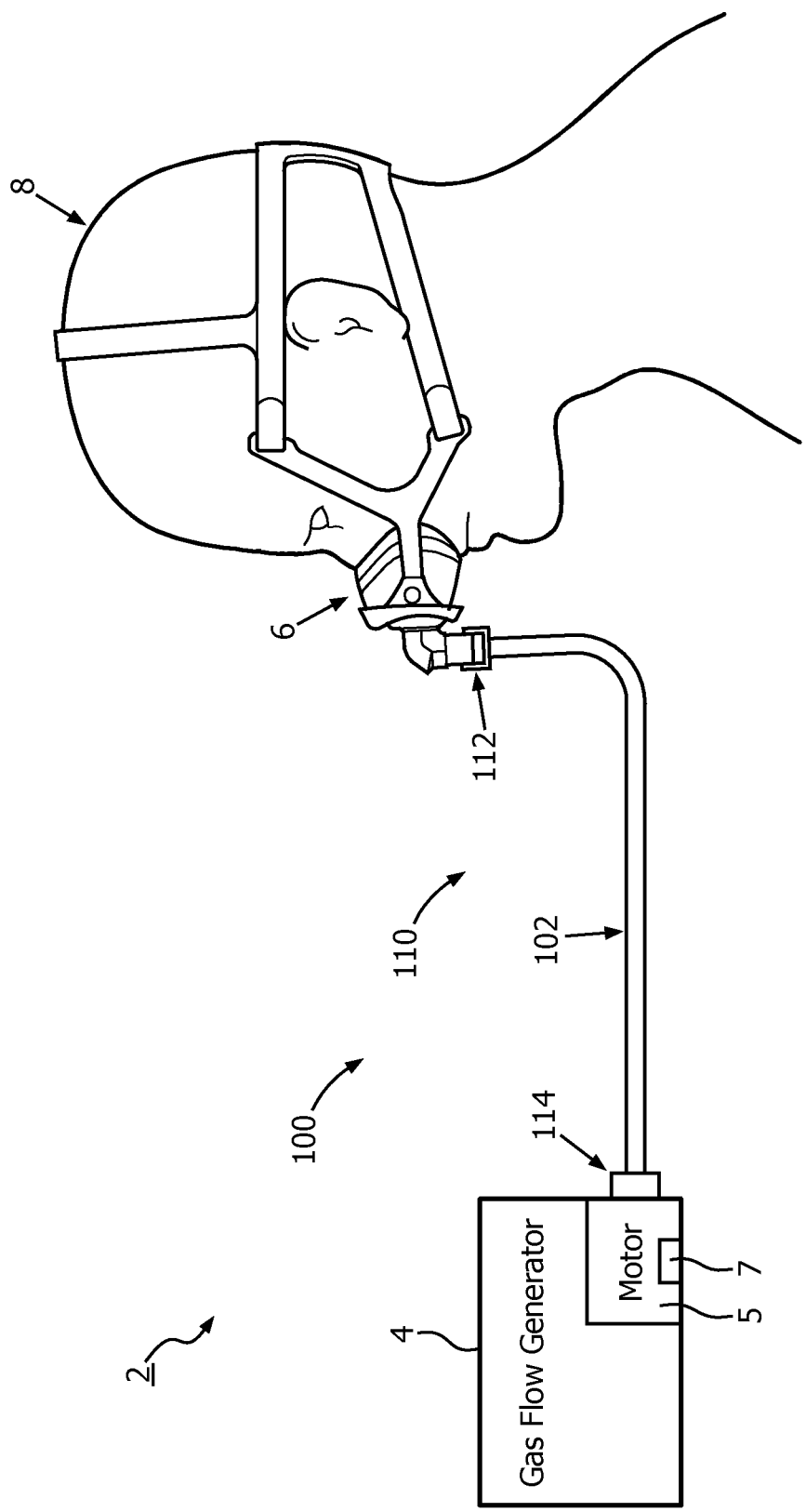
FIG. 1 is a simplified view of a pressure support system according to one particular, non-limiting embodiment in which the present invention may be implemented.

FIG. 1 shows a simplified view of a pressure support system 2 according to an exemplary embodiment. As shown, pressure support system 2 includes a gas flow generator 4, a patient interface device 6 fluidly coupled to gas flow generator 4, and an interconnect assembly 100. In operation, patient interface device 6 is secured to a patient 8, and gas flow generator 4 produces a flow of breathing gas for patient 8. Interconnect assembly 100 includes a conduit (patient circuit) 102 and an adjustment assembly 110. Conduit 102 is fluidly coupled to gas flow generator 4 and patient interface device 6, thereby allowing the breathing gas to pass from gas flow generator 4 to patient interface device 6. In accordance with the disclosed concept, adjustment assembly 110 quickly and easily allows the length of conduit 102 to be decreased, increased, and maintained in a predetermined position. Thus, when the length of conduit 102 is decreased and maintained in the decreased position, packing and transporting pressure support system 2 is advantageously simplified. Furthermore, pressure support therapy is able to be supplied when the length of conduit 102 is in the decreased position. When the length of conduit 102 needs to be increased, adjustment assembly 110 allows conduit 102 to be lengthened. In this manner, the length of conduit 102 is customizable (i.e., able to be set to a predetermined length depending on the preference of patient 8).

Referring to FIG. 2 and FIG. 3, conduit 102 has a central lumen 103, a first end 104, and a second end 106. Adjustment assembly 110 includes a coupling member 112, a winding apparatus 114, and a number of tension members (two tension members 116, 118 are shown). First end 104 of conduit 102 is coupled to coupling member 112. Second end 106 of conduit 102 is coupled to winding apparatus 114. As shown in FIG. 1, coupling member 112 is coupled to patient interface device 6, and winding apparatus 114 is coupled to gas flow generator 4. Tension members 116, 118 extend through central lumen 103 and partially overlay conduit 102. As will be discussed in greater detail below, tension members 116, 118 move independently with respect to conduit 102 in order to allow the length of conduit 102 to change. Additionally, tension members 116, 118 advantageously have a relatively large tensile strength to diameter ratio. In this manner, pressure drops associated with tension members 116, 118 extending through central lumen 103 are advantageously minimized.

Tension members 116, 118 are connected to winding apparatus 114 at a first end thereof. In the example of FIG. 2 and FIG. 3, tension members 116, 118 are anchored (i.e., fixedly connected) to coupling member 112 at an opposing end by being overmolded with coupling member 112. However, it is within the scope of the disclosed concept for tension members 116, 118 to be anchored (i.e., fixedly connected) at the opposing second end by any suitable alternative mechanism. For example, tension members 116, 118 may be encased between threaded components (not shown), or encased between components (not shown) that are connected by a snap-fit mechanism. Tension members 116, 118 may also be glued to coupling member 112 and/or first end 104 of conduit 102. Alternatively, tension members 116, 118 may be fed through a hole (not shown) in coupling member 112 and/or first end 104 of conduit 102 and then secured to an opposing external portion.

Figure 4:
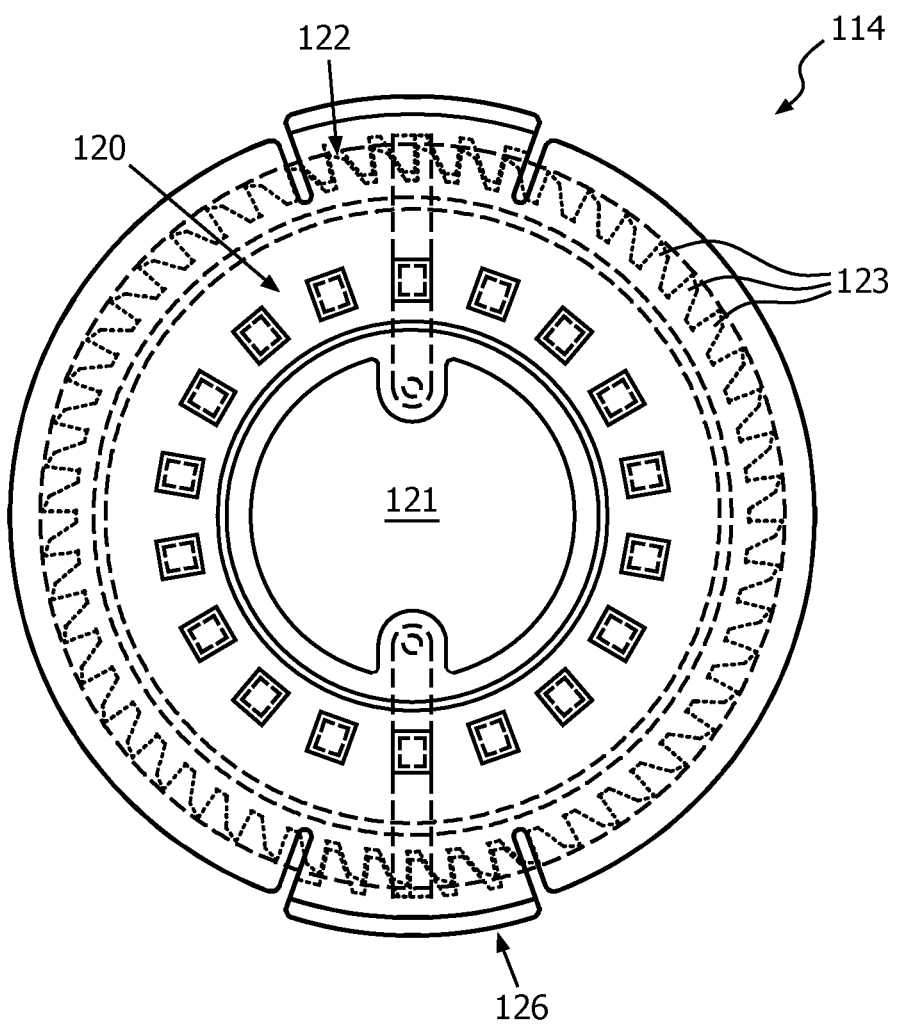
FIG. 4 is a top plan view of a winding apparatus for the interconnect assembly of FIG. 2 and FIG. 3.

Winding apparatus 114 includes a spool 120, a gear member 122, a spring 124, and a ratchet portion 126. As shown in FIG. 4, gear member 122 has a central lumen 121 and in operation, central lumen 121 receives the flow of breathing gas produced by gas flow generator 4 (FIG. 1). In other words, winding apparatus 114 does not obstruct the flow of breathing gas between gas flow generator 4 (FIG. 1) and patient interface device 6 (FIG. 1). Ratchet portion 126 engages spool 120 and allows winding apparatus 114 to wind and unwind, as will be discussed below. Spring 124 is coupled to spool 120 and forces spool 120 into ratchet portion 126 in order to add tension during winding and unwinding of winding apparatus 114. As shown in FIG. 2, tension members 116, 118 are fed through winding apparatus 114 and are connected to spool 120 of winding apparatus 114.

In operation, winding apparatus 114 winds tension members 116, 118, which move independently with respect to conduit 102 in order to move conduit 102 from a first position, shown in FIG. 2, to a second position, shown in FIG. 3. More specifically, because tension members 116, 118 are anchored (i.e., fixedly connected) to coupling member 112, and conduit 102 is coupled to coupling member 112, when winding apparatus 114 winds tension members 116, 118 onto spool 120, coupling member 112 pulls first end 104 of conduit 102 toward second end 106 of conduit 102.

As shown in FIG. 2, when conduit 102 is in the first position (i.e., before being wound by the winding apparatus 114), conduit 102 has a first length 130. Referring to FIG. 3, when conduit 102 is in the second position (i.e., after winding apparatus 114 has wound tension members 116, 118 onto spool 120), conduit 102 has a second length 132 that is less than first length 130. In other words, when winding apparatus 114 winds tension members 116, 118, the length of conduit 102 decreases. As a result, packing and transporting pressure support system 2 (FIG. 1) is advantageously simplified, and pressure support therapy may be supplied when conduit 102 is at any shortened length. Additionally, winding apparatus 114 is configured to maintain conduit 102 in the second position (FIG. 3).

More specifically, and with reference to FIG. 4, ratchet portion 126 engages spool 120 and maintains spool 120 in a given position until ratchet portion 126 releases gear member 122. When ratchet portion 126 is being wound around gear member 122, ratchet portion 126 oscillates as each tooth (see, for example, teeth 123 in FIG. 4) of gear member 122 passes and prevents the teeth 123 from reversing direction (i.e., unwinding of spool 120). When ratchet portion 126 is squeezed in a direction 127 (see FIG. 3), gear member 122 is released. When gear member 122 is released, spool 120 and ratchet portion 126 may unwind, thereby allowing the length of conduit 102 to increase. As a result, the length of conduit 102 is advantageously able to be decreased, increased, and maintained in a predetermined position.

Referring again to FIG. 1, gas flow generator 4 includes a motor 5 that drives winding apparatus 114. In operation, patient 8 may activate motor 5 by pressing a button 7, thereby allowing conduit 102 to retract or increase to a predetermined length. It is, however, within the scope of the disclosed concept for winding apparatus 114 to be driven by any suitable alternative mechanism instead of a motor in order to perform the desired function of winding tension members 116, 118 onto spool 120 (e.g., pneumatic mechanism, spring mechanism, being manually wound). Additionally, the disclosed concept has been described in association with coupling member 112 being coupled to patient interface device 6 and winding apparatus 114 being coupled to gas flow generator 4. However, it is within the scope of the disclosed concept to employ any suitable alternative configuration in order to perform the desired function of moving conduit 102 to a second position and maintaining conduit 102 in the second position.

Figure 5:
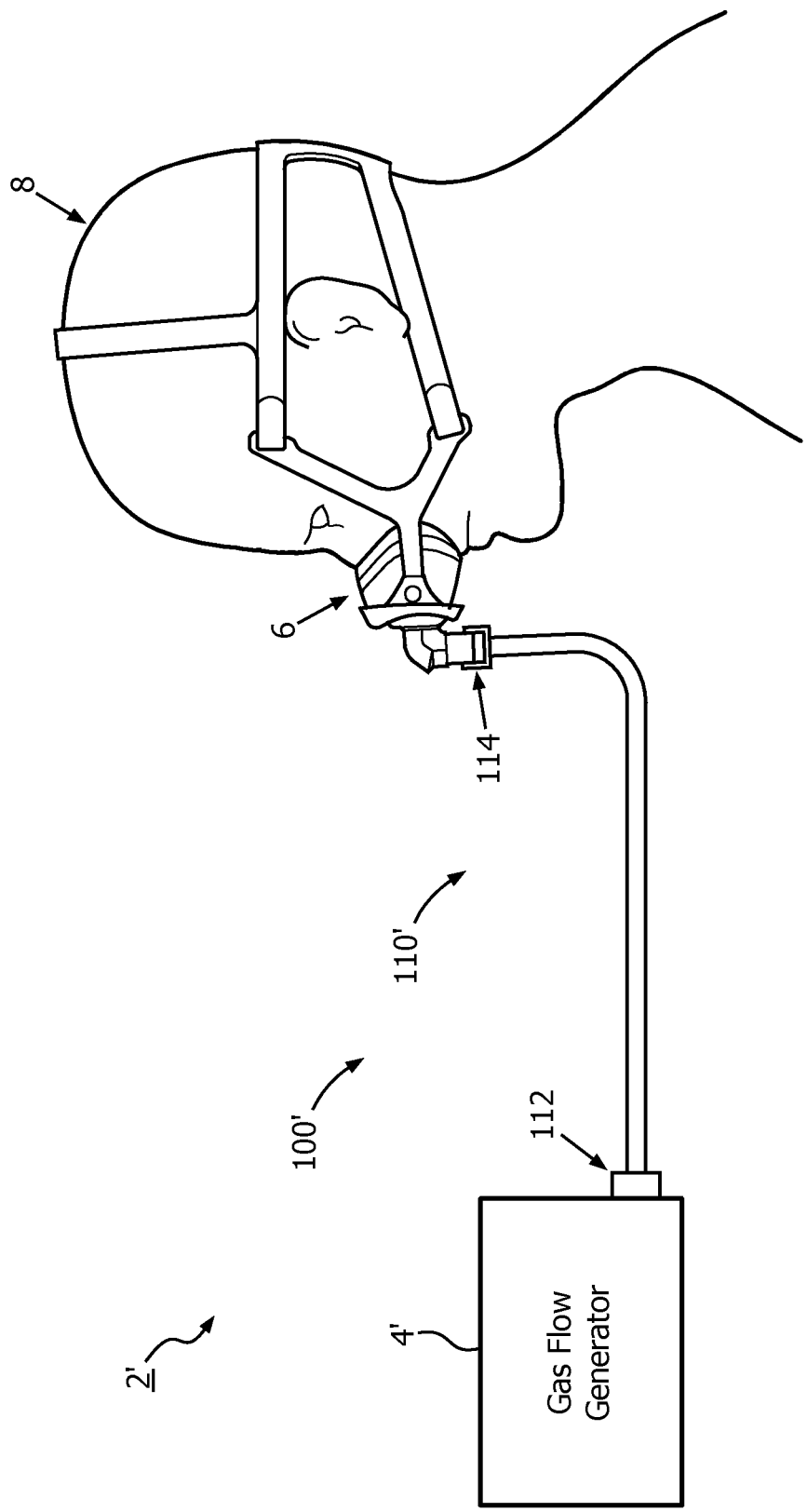
FIG. 5 shows a simplified view of another pressure support system in accordance with an alternative embodiment of the disclosed concept.

For example, FIG. 5 shows a pressure support system 2' in accordance with an alternative embodiment of the disclosed concept. As shown, pressure support system 2' includes an interconnect assembly 100' that has an adjustment assembly 110'. Adjustment assembly 110' includes coupling member 112 and winding apparatus 114. Coupling member 112 is coupled to a gas flow generator 4', and winding apparatus 114 is coupled to patient interface device 6. It is also within the scope of the disclosed concept to employ one or multiple winding apparatus (not shown) at any point on conduit 102 (e.g., not necessarily at the distal ends) in order to move conduit 102 to a second position and maintain conduit 102 in the second position. Furthermore, winding apparatus 114, or a similar suitable alternative winding apparatus (not shown) may be spaced from conduit 102 (e.g., without limitation, located entirely inside an alternative gas flow generator (not shown) and not structured to receive the flow of breathing gas).

FIG. 6 and FIG. 8 show another interconnect assembly 200 that may be implemented in pressure support system 2 (FIG. 1) in place of interconnect assembly 100. As shown, interconnect assembly 200 includes a conduit (e.g., extruded body 202) and an adjustment assembly 210. Extruded body 202 has an inner surface 201, an outer surface 205, and a number of chambers (two chambers 207, 209 are shown in FIG. 7) located between inner surface 201 and outer surface 205. Chambers 207, 209 preferably extend the entire length of extruded body 202. Adjustment assembly 210 includes a coupling member 212, a winding apparatus 214, and a number of tension members 216, 218. Tension member 218 extends through chamber 207 and tension member 216 extends through chamber 209. Thus, tension members 216, 218 at least partially overlay extruded body 202. Tension members 216, 218 are anchored (i.e., fixedly connected) to coupling member 212 at one end. In the example of FIG. 6 and FIG. 8, tension members 216, 218 are anchored (i.e., fixedly connected) to coupling member 212 by being overmolded with coupling member 212. However, tension members 216, 218 may be anchored by any suitable alternative mechanism, such as those described hereinabove in association with tension members 116, 118 (FIG. 2 and FIG. 3) and coupling member 112 (FIG. 1-FIG. 3, and FIG. 5).

Tension members 216, 218 are connected with winding apparatus 214 at an opposing end. It will be appreciated with reference to FIG. 6 and FIG. 8 that winding apparatus 214 is structured to wind and unwind tension members 216, 218 in substantially the same manner in which winding apparatus 114 (FIG. 1 through FIG. 5) winds tension members 116, 118 (FIG. 2 and FIG. 3) in order to adjust the length of extruded body 202. Furthermore, when tension members 216, 218 are being wound and unwound, chambers 207, 209 (FIG. 7) advantageously allow tension members 216, 218 to move independently with respect to extruded body 202. Thus, FIG. 6 shows interconnect assembly 200 with extruded body 202 in a first position (i.e., before winding apparatus 214 has wound tension members 216, 218) and FIG. 8 shows interconnect assembly 200 with extruded body 202 in a second position (i.e., after winding apparatus 214 has wound tension members 216, 218). In addition, winding apparatus 214 allows extruded body 202 to be maintained in the second position (FIG. 8), and also released from the second position (FIG. 8) in order to be lengthened (see, for example, discussion above with respect to winding apparatus 114 maintaining conduit 102 in the second position and releasing conduit 102). Accordingly, advantages associated with interconnect assembly 100 likewise apply to interconnect assembly 200.

FIG. 9 and FIG. 11 show another interconnect assembly 300 that may be implemented in pressure support system 2 (FIG. 1) in place of interconnect assembly 100 (FIG. 1). As shown, interconnect assembly 300 includes a conduit 302 and an adjustment assembly 310. Adjustment assembly 310 includes a number of guide members (three guide members 311, 313, 315 are shown), a coupling member 312, a winding apparatus 314, and a number of tension members (two tension members 316, 318 are shown). Conduit 302 has an outer surface 305. Guide members 311, 313, 315 are each coupled to outer surface 305, preferably through a snap-fit mechanism or a compression-fit mechanism. FIG. 10 shows a side view of guide member 315. As shown, guide member 315 includes a number of thru holes 315-1, 315-2. It will be appreciated that guide members 311, 313 likewise include a corresponding number of thru holes. Tension member 318 extends through thru hole 315-1 and the corresponding thru holes of guide members 311, 313. Tension member 316 extends through thru hole 315-2 and the corresponding thru holes of guide members 311,313. Thus, tension members 316, 318 at least partially overlay conduit 302.

Tension members 316, 318 are anchored (i.e., fixedly connected) to coupling member 312 at one end. In the example of FIG. 9 and FIG. 11, tension members 316, 318 are anchored (i.e., fixedly connected) to coupling member 312 by being overmolded with coupling member 312. However, tension members 316, 318 may be anchored by any suitable alternative mechanism, such as described hereinabove in association with tension members 116, 118, 216, 218 (FIG. 2, FIG. 3, FIG. 6 and FIG. 8) and respective coupling members 112, 212 (FIG. 1 through FIG. 3, FIG. 5, FIG. 6 and FIG. 8). Tension members 316, 318 are connected with winding apparatus 314 at an opposing end.

In operation, winding apparatus 314 is structured to wind tension members 316, 318 in substantially the same manner as described hereinabove in association with interconnect assemblies 100, 200. Additionally, because tension members 316, 318 are located external with respect to conduit 302, when tension members 316, 318 are being wound and unwound, guide members 311, 313, 315 advantageously protect tension members 316, 318 from becoming tangled. Thus, when winding apparatus 314 winds tension members 316, 318, the length of conduit 302 decreases from a first position, shown in FIG. 9, to a second position, shown in FIG. 11. Additionally, winding apparatus 314 is structured to maintain conduit 302 in the second position (FIG. 11), and also release and thereby lengthen conduit 302 (see, for example, discussion above with respect to winding apparatus 114 maintaining conduit 102 in the second position and releasing conduit 102). Accordingly, advantages associated with interconnect assemblies 100, 200 likewise apply to interconnect assembly 300.

Referring again to FIG. 2 and FIG. 3, conduit 102 includes a membrane portion 102-1 and a helix portion 102-2 wrapped on membrane portion 102-1. Similarly, as shown in FIG. 9 and FIG. 11, conduit 302 includes a membrane portion 302-1 and a helix portion 302-2 wrapped on membrane portion 302-1. It will be appreciated that adjustment assembly 110 and adjustment assembly 310 may be implemented with any suitable alternative conduit (e.g., without limitation, extruded body 202 (FIG. 6 and FIG. 8)) in order to perform the desired function of moving the conduit from a first position to a second position, as described herein.

Accordingly, it will be appreciated that the disclosed concept provides for an improved (e.g., without limitation, easier to transport, able to be customized, and able to deliver pressure support therapy with a conduit at any length) interconnect assembly 100, 200, 300 and pressure support system 2, 2' including the same, which among other benefits, allows the length of conduit 102, 202, 302 to be quickly and easily decreased, increased, and maintained in a predetermined position.

While specific embodiments of the disclosed concept have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the disclosed concept which is to be given the full breadth of the claims appended and any and all equivalents thereof.

What is claimed is:

1. An interconnect assembly for a pressure support system, the pressure support system comprising a gas flow generator and a patient interface device fluidly coupled to the gas flow generator, the gas flow generator being structured to produce a flow of breathing gas for a patient, the interconnect assembly comprising:
   a conduit having a first end structured to be coupled to the gas flow generator and a second end structured to be coupled to the patient interface device, the conduit having a length; and
   an adjustment assembly comprising:
      a number of tension members each at least partially overlaying the conduit and being coupled to each of the first end and the second end, each of the tension members being structured to move independently with respect to the conduit, and
      a winding apparatus connected to each of the tension members, the winding apparatus being structured to wind each of the tension members, wherein, when the winding apparatus winds the tension members, the length of the conduit decreases, and wherein the winding apparatus comprises a lumen for receiving breathing gas produced by the gas flow generator.

2. The interconnect assembly of claim 1, wherein the conduit has a central lumen, and wherein each of the tension members extends through the central lumen.

3. The interconnect assembly of claim 1, wherein the conduit has an inner surface and an outer surface, and wherein each of the tension members is disposed between the inner surface and the outer surface.

4. The interconnect assembly of claim 3, wherein the conduit is an extruded body, wherein the extruded body has a number of chambers, wherein each of the chambers extends from the first end to the second end, and wherein each of the tension members extends through a corresponding one of the chambers.

5. The interconnect assembly of claim 1, wherein the conduit has an outer surface, wherein the adjustment assembly further comprises a number of guide members each coupled to the outer surface of the conduit, wherein each of the guide members has a number of thru holes, and wherein each of the tension members extends through a corresponding one of the thru holes of each of the guide members.

6. The interconnect assembly of claim 5, wherein the number of guide members is a plurality of guide members, and wherein each of the plurality of guide members is coupled to the outer surface of the conduit by a mechanism selected from the group consisting of a snap-fit mechanism and a compression-fit mechanism.

7. The interconnect assembly of claim 1, wherein the adjustment assembly further comprises a coupling member, wherein the coupling member is coupled to the first end of the conduit, and wherein each of the tension members is fixedly connected to the coupling member.

8. The interconnect assembly of claim 7, wherein the winding apparatus is coupled to the second end of the conduit, wherein, when the winding apparatus winds the tension members, the conduit moves from a first position to a second position, and wherein the winding apparatus is structured to maintain the conduit in the second position.

9. The interconnect assembly of claim 8, wherein the winding apparatus comprises a spool, a gear member, a spring, and a ratchet portion wherein, when the conduit moves from the first position to the second position, each of the tension members winds on the spool, wherein the gear member comprises the winding apparatus lumen, wherein the lumen is structured to receive the flow of breathing gas, wherein the gear member engages the spool, wherein the spring is coupled to the spool, and wherein the spring forces the spool into the ratchet portion.

10. The interconnect assembly of claim 1, wherein the adjustment assembly further comprises a coupling member, wherein the coupling member is coupled to the second end of the conduit, wherein each of the tension members is fixedly connected to the coupling member, and wherein the winding apparatus is coupled to the first end of the conduit.

11. The interconnect assembly of claim 1, wherein the number of tension members is a plurality of tension members.

12. A pressure support system comprising:
(a) a gas flow generator structured to produce a flow of breathing gas for a patient (8);
(b) a patient interface device fluidly coupled to the gas flow generator; and
(c) an interconnect assembly comprising:
  (1) a conduit having a first end coupled to the gas flow generator and a second end couple to the patient interface device, the conduit having a length, and
  (2) an adjustment assembly comprising:
    (i) a number of tension members each at least partially overlaying the conduit and being coupled to each of the first end and the second end, each of the tension members being structured to move independently with respect to the conduit, and
    (ii) a winding apparatus connected to each of the tension members, the winding apparatus being structured to wind each of the tension members, wherein, when the winding apparatus winds the tension members, the length of the conduit decreases, and wherein the winding apparatus comprises a lumen for receiving breathing gas produced by the gas flow generator.

13. The pressure support system of claim 12, wherein the winding apparatus is coupled to the gas flow generator, wherein the gas flow generator comprises a motor, and wherein the motor is structured to drive the winding apparatus.

14. The pressure support system of claim 12, wherein the adjustment assembly further comprises a coupling member, wherein the coupling member is coupled to the second end of the conduit, and wherein each of the tension members is fixedly connected to the coupling member.

15. A method of customizing a pressure support system comprising the steps of:
(a) providing the pressure support system, the pressure support system comprising:
  (1) a gas flow generator structured to produce a flow of breathing gas for a patient,
  (2) a patient interface device fluidly coupled to the gas flow generator; and
  (3) an interconnect assembly comprising:
    (i) a conduit having a first end coupled to the gas flow generator and a second end coupled to the patient interface device, the conduit being structured to move between a first position and a second position, the conduit having a first length in the first position and a second length in the second position, the second length being less than the first length, and
    (ii) an adjustment assembly comprising:
      (A) a number of tension members and being coupled to each of the first end and the second end, each of the tension members being structured to move independently with respect to the conduit, and
      (B) a winding apparatus connected to each of the tension members, the winding apparatus being structured to wind each of the tension members wherein the winding apparatus comprises a lumen for receiving breathing gas produced by the gas flow generator,
(b) winding each of the tension members with the winding apparatus in order to move the conduit from the first position to the second position; and
(c) maintaining the conduit in the second position.

* * * * *